(12) United States Patent
Tan et al.

(10) Patent No.: US 7,382,866 B2
(45) Date of Patent: Jun. 3, 2008

(54) X-RAY IMAGING APPARATUS

(75) Inventors: Yongtao Tan, Beijing (CN); Chen Zhang, Beijing (CN); Yuqing Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 29 days.

(21) Appl. No.: 11/498,115

(22) Filed: Aug. 2, 2006

(65) Prior Publication Data
US 2006/0268409 A1  Nov. 30, 2006

(30) Foreign Application Priority Data
Apr. 8, 2005  (CN) .................. 2005 1 0091708

(51) Int. Cl.
*G21K 1/02* (2006.01)
(52) U.S. Cl. ...................................... 378/147; 378/206
(58) Field of Classification Search ........ 378/145–153, 378/156–160, 204–206
See application file for complete search history.

(56) References Cited

U.S. PATENT DOCUMENTS
5,080,100 A * 1/1992 Trotel .......................... 600/407
2005/0069092 A1  3/2005 Xiaodong et al.

FOREIGN PATENT DOCUMENTS
DE  102004046035 A1  4/2005
JP  2005-103244  4/2005

* cited by examiner

*Primary Examiner*—Courtney Thomas
(74) *Attorney, Agent, or Firm*—Armstrong Teasdale LLP

(57) ABSTRACT

With a view to providing an X-ray imaging apparatus having a projector-collimator capable of adjusting an irradiation position of a light beam easily and accurately, a first luminous flux is made a luminous flux present within an orthogonal plate orthogonal to a y-axis direction which is an orthogonal direction and a second luminous flux present within the orthogonal plane is reflected and moved within the orthogonal plane to produce a light beam. Consequently, an irradiation position of the light beam over a subject can be adjusted in an independent manner by movement Δy in the orthogonal direction with use of a first screw and movement Δx within the orthogonal plane with use of a second crew. As a result, adjustment of an X-ray irradiation field position by an operator can be effected not only easily but also with a high accuracy.

20 Claims, 7 Drawing Sheets

X-RAY IMAGING APPARATUS

CROSS REFERENCE TO RELATED APPLICATIONS

This application claims the benefit of Chinese Application No. 200510091708.3 filed Aug. 4, 2005.

BACKGROUND OF THE INVENTION

The present invention relates to an X-ray imaging apparatus having a projector-collimator installed within a movable diaphragm to project a light beam to an irradiation field position of X-ray on a subject.

In recent radiographing using an X-ray imaging apparatus, a light beam is radiated onto a subject to be radiographed. An operator checks the position of the light beam visually and thereby confirms and determines an X-ray irradiation position. In this way the operator is sure to radiate X-ray to a desired region on the subject while preventing the radiation of X-ray to an unnecessary region.

The projector-collimator for emitting the light beam is disposed in the interior of a movable diaphragm which restricts the irradiation field of X-ray. The projector-collimator changes the irradiation range of the light beam in interlock with the movable diaphragm changing an aperture to change the X-ray irradiation field (see, for example, Non-Patent Literature 1).

It is necessary that the X-ray irradiation field and the position of the light beam be coincident with each other accurately. The operator makes adjustment so that the irradiation position of the light beam becomes coincident with the X-ray irradiation field. On the other hand, the projector-collimator conducts a luminous flux emitted from a light source to the X-ray irradiation field through plural mirrors. At this time, the positions or inclinations of these mirrors are adjusted to adjust the position of the light beam on the subject.

[Non-Patent Literature 1] Tetsuo OKABE, et al., "Radio-diagnosis Device Engineering," Ishiyaku Publishers, Inc., Oct. 1, 1997, pp. 336-338

According to the above background art, however, the adjustment of the light beam position on the subject is difficult to perform and is inferior in point of accuracy. More particularly, the position of the light beam on the subject which beam is guided through plural mirrors is changed in interlock with movement of those mirrors. However, the change in position of the light beam is correlated with all of the mirrors and therefore it is necessary to adjust the plural mirrors simultaneously.

Particularly, in the case where the light beam radiated from the projector-collimator is a frame line which clearly shows a frame of the irradiation field of X-ray, it is necessary that strain or the like of the light beam be also taken into account. This is a cause of making the adjustment of light beam more difficult.

SUMMARY OF THE INVENTION

Thus, it is important how an X-ray imaging apparatus having a projector-collimator capable of adjusting the light beam irradiation position easily and that accurately is to be provided.

The present invention has been accomplished for solving the above-mentioned problem involved in the background art and it is an object of the invention to provide an X-ray imaging apparatus having a projector-collimator capable of adjusting the light beam irradiation position easily and accurately.

For solving the above-mentioned problem and achieving the above-mentioned object, in a first aspect of the present invention there is provided an X-ray imaging apparatus comprising: an X-ray source for radiating X-ray to a subject; a movable diaphragm for adjusting an irradiation field of the X-ray; and a projector-collimator installed within the movable diaphragm to project a light beam to an irradiation field position on the subject, wherein the projector-collimator comprises: a first reflecting section which is positioned outside the irradiation field, produces a first luminous flux in an orthogonal direction orthogonal to the X-ray radiating direction, and reflects the first luminous flux within an orthogonal plane orthogonal to the orthogonal direction to produce a second luminous flux; and a second reflecting section which reflects the second luminous flux in the direction of the irradiation field within the orthogonal plane to produce of third luminous flux, and reflects the third luminous flux in the X-ray radiating direction inside the irradiation field within the orthogonal plane to produce the light beam.

According to this first aspect of the present invention, by the first reflecting section in the projector-collimator, a first luminous flux is produced outside the irradiation field and in an orthogonal direction orthogonal to the X-ray radiating direction and is reflected within an orthogonal plane orthogonal to the orthogonal direction to produce a second luminous flux, then by the second reflecting section in the projector-collimator, the second luminous flux is reflected in the direction of the irradiation field within the orthogonal plane to produce a third luminous flux and the third luminous flux is reflected in the irradiation direction within the irradiation field to produce a light beam.

In a second aspect of the present invention there is provided, in combination with the above first aspect, an X-ray imaging apparatus wherein the first reflecting section comprises a light source for producing the first luminous flux, a first mirror for producing the second luminous flux from the first luminous flux, and a first base for disposing the light source and the first mirror thereon.

According to this second aspect of the present invention, the first reflecting section comprises a light source and a first mirror both disposed on a first base.

In a third aspect of the present invention there is provided, in combination with the above second aspect, an X-ray imaging apparatus wherein the light source is a halogen lamp.

According to this third aspect of the present invention, since the light source is a halogen lamp, it has a long service life and is stable.

In a fourth aspect of the present invention there is provided, in combination with the above second or third aspect, an X-ray imaging apparatus wherein the first base includes moving means for moving the first mirror in the orthogonal direction.

According to this fourth aspect of the present invention, the first base causes the orthogonal plane including the second luminous flux to move in the orthogonal direction.

In a fifth aspect of the present invention there is provided, in combination with the above fourth aspect, an X-ray imaging apparatus wherein moving means includes a first screw for changing relative positions in the orthogonal direction of the first base and a mirror support plate for supporting the first mirror.

According to this fifth aspect of the present invention, the moving means causes the first mirror on the first base to move in the orthogonal direction with use of the first screw.

In a sixth aspect of the present invention there is provided, in combination with the above fourth or fifth aspect, an X-ray imaging apparatus wherein the moving means, during the movement, does not change the inclination of the first mirror in the orthogonal direction.

According to this sixth aspect of the present invention, the moving means causes the first mirror to move while keeping constant the reflecting direction of the second luminous flux.

In a seventh aspect of the present invention there is provided, in combination with any of the above first to sixth aspects, an X-ray imaging apparatus wherein the second reflecting section comprises a second mirror for producing the third luminous flux from the second luminous flux, a third mirror for producing the light beam from the third luminous flux and transmitting the X-ray, and a second base for disposing the second and third mirrors fixedly thereon.

According to this seventh aspect, the second base conducts the second luminous flux into the X-ray irradiation field to produce a light beam.

In an eighth aspect of the present invention there is provided, in combination with the above seventh aspect, an X-ray imaging apparatus wherein the second base includes rotating means for performing a slight rotation around the orthogonal direction.

According to this eighth aspect of the present invention, the second base causes the light beam to move within the orthogonal plane with use of rotating means.

In a ninth aspect of the present invention there is provided, in combination with the above eighth aspect, an X-ray imaging apparatus wherein the rotating means includes a second screw for changing relative positions of the second base and the first base.

According to this ninth aspect of the present invention, the rotating means causes the second base to rotate around the orthogonal direction with use of a second screw.

In a tenth aspect of the present invention there is provided, in combination with any of the above seventh to ninth aspects, an X-ray imaging apparatus wherein the second mirror includes a reflecting surface for the second luminous flux positioned outside the irradiation field.

According to this tenth aspect of the present invention, the second mirror does not exert any influence on the X-ray which is radiated to the subject.

In an eleventh aspect of the present invention there is provided, in combination with any of the above seventh to tenth aspects, an X-ray imaging apparatus wherein the third mirror includes a reflecting surface for reflecting the third luminous flux at a size and position including the X-ray irradiation field.

According to this eleventh aspect of the present invention, the third mirror not only produces a light beam but also transmits X-ray.

In a twelfth aspect of the present invention there is provided, in combination with any of the above seventh to eleventh aspects, an X-ray imaging apparatus wherein the second and third mirrors are disposed in parallel with each other.

According to this twelfth aspect of the present invention, the second and third mirrors reflect the light beam in a direction parallel to the second luminous flux.

In a thirteenth aspect of the present invention there is provided, in combination with any of the above seventh to twelfth aspects, an X-ray imaging apparatus wherein the second and third mirrors have each a rectangular shape having long sides in the orthogonal direction.

According to this thirteenth aspect of the present invention, the second and third mirrors make a movable range wide in the orthogonal direction of the first mirror.

In a fourteenth aspect of the present invention there is provided, in combination with any of the above second to sixth aspects, an X-ray imaging apparatus wherein the projector-collimator includes a third base for supporting the first and second bases.

According to this fourteenth aspect of the present invention, the projector-collimator, with use of the third base, facilitates the mounting of the first and second bases within the movable diaphragm.

In a fifteenth aspect of the present invention there is provided, in combination with the above fourteenth aspect, an X-ray imaging apparatus wherein the second base includes a rotary shaft extending in the orthogonal direction and supported by the third base.

According to this fifteenth aspect of the present invention, the second base is made rotatable with respect to the third base.

In a sixteenth aspect of the present invention there is provided, in combination with the above fourteenth or fifteenth aspect, an X-ray imaging apparatus wherein the first base is fixed to the third base.

According to this sixteenth aspect, the first base fixes the position of the first luminous flux relative to the third base.

According to the present invention, the projector-collimator, using the first reflecting section, causes the first luminous flux to be a luminous flux present within an orthogonal plane orthogonal to the orthogonal direction and, using the second reflecting section, causes the second luminous flux to reflect and move within the orthogonal plane. Therefore, by movement in the orthogonal direction of the orthogonal plane including the luminous flux and by rotation of the orthogonal plane, the light beam irradiation position on the subject can be adjusted independently in the orthogonal direction and in the intra-orthogonal plane direction. Consequently, it is possible to not only facilitate the adjustment but also make the adjustment highly accurate.

Further objects and advantages of the present invention will be apparent from the following description of the preferred embodiments of the invention as illustrated in the accompanying drawings.

DETAILED DESCRIPTION OF THE INVENTION

With reference to the accompanying drawings, the following description is provided about a best mode for carrying out the present invention with respect to an X-ray imaging apparatus. The present invention is not limited to the following embodiment.

Figure 1:
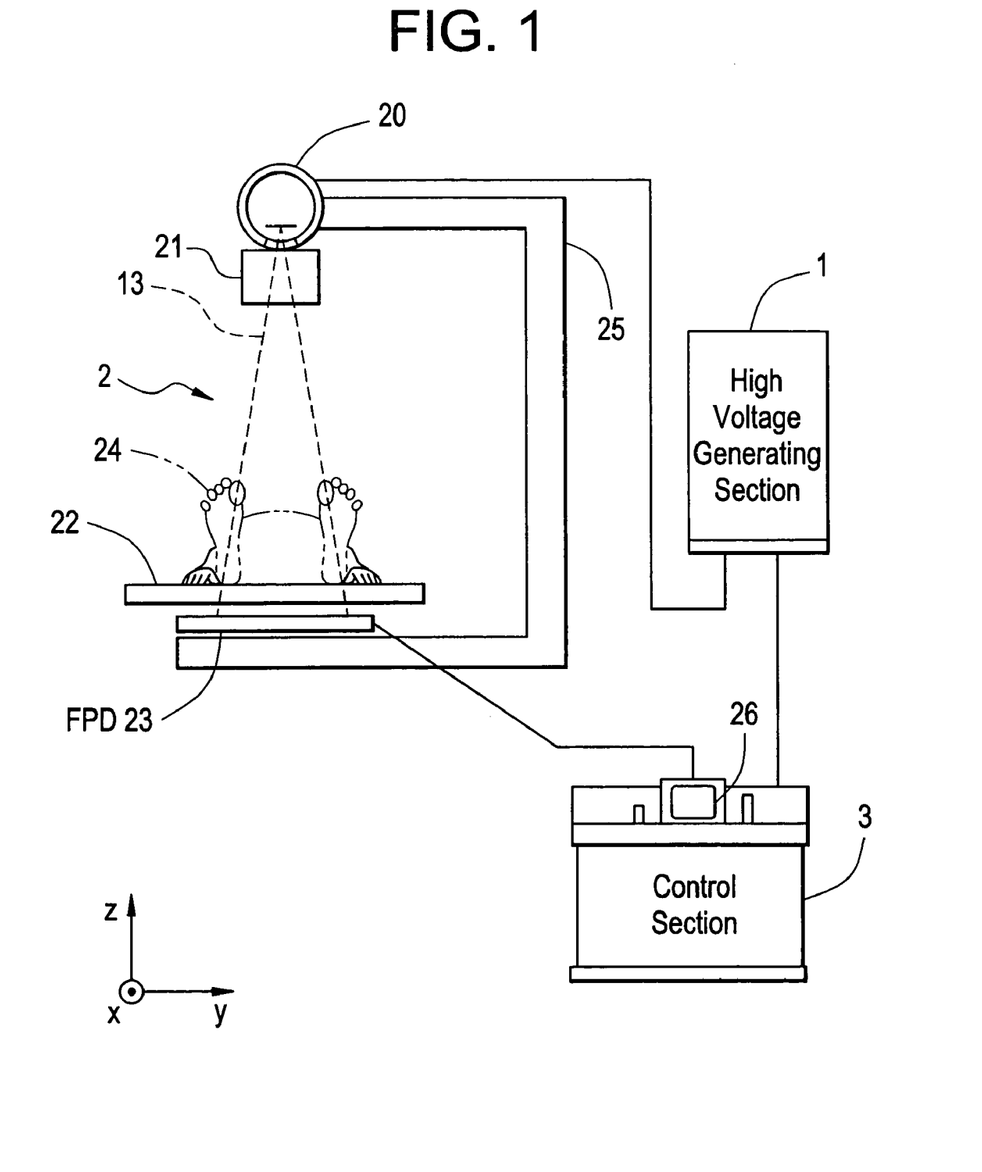
FIG. 1 is a block diagram showing an entire construction of an X-ray imaging apparatus.

Reference will first be made to the entire construction of an X-ray imaging apparatus according to an embodiment of the present invention. FIG. 1 illustrates an entire construction of an X-ray imaging apparatus according to this embodiment. The X-ray imaging apparatus includes a high voltage generating section 1, a C arm section 2 and a control section 3. The high voltage generating section 1 and the C arm section 2 are connected together through a power cable. Further, the C arm section 2 and the control section 3 are connected together through a communication cable. Further, x-y-z coordinate axes shown in FIG. 1 are the same as those shown in the drawings which follow, clearly indicating a positional relation among the drawings.

In the high voltage generating section, a high voltage to be fed to an X-ray tube, which voltage is about 20 to 50 kV.

The C arm section 2 includes an X-ray source 20, a movable diaphragm 21, a top board 22, an FPD (Flat Panel Detector) 23 and an arm 25. The X-ray source 20 comprises an X-ray tube and is supplied with electric power from the high voltage generating section 1. In accordance with instructions provided from the control section 3 the X-ray source 20 emits X-ray to the subject 24 positioned in the z-axis direction.

The movable diaphragms 21 diaphragms linear cone restriction blades containing lead as a main component to restrict the irradiation field. X-ray which is emitted from the X-ray source 20 and whose irradiation field has been restricted by the movable diaphragm 21 forms an irradiation path indicated by a linear cone 13. As indicated by a dotted line in FIG. 1, the linear cone 13 is in the shape of a cone with a focal position of the X-ray source 20 as a vertex. A projector-collimator is disposed in the movable diaphragm 21. An operator projects a light beam to an X-ray irradiation field on a subject 24 and performs an accurate X-ray irradiation for a desired position. As to the movable diaphragm 21, a description will be given later.

The top board 22 is for placing thereon the subject 24 in a lying-down condition. It causes the subject 24 to be disposed at an optimum radiographing position manually or automatically.

The FPD 23 has a two-dimensional matrix-like sensor cell, the sensor cell including a scintillator for converting the X-ray which has passed through the subject 24 into light and a photodiode for detecting the light.

An electric charge output of a sensor cell which constitutes a unit pixel is read out using a switching element such as TFT (thin film transistor) and is used as image information.

The X-ray source 20 and the FRD 23 are disposed in opposition to each other through the arm 25 in a sandwiching relation to the subject 24, whereby the operator is sure to acquire transmitted image information of the subject 24. In the C arm section, there are selected height and angle best suited to radiographing by turning or height adjustment through a support portion (not shown).

The control section 3 includes a control computer and an image display 26 and is connected to the high voltage generating section 1 and the C arm section 2 electrically through cables. The control section 3 controls the irradiation of X-ray and the acquisition of transmitted image information.

Figure 2:
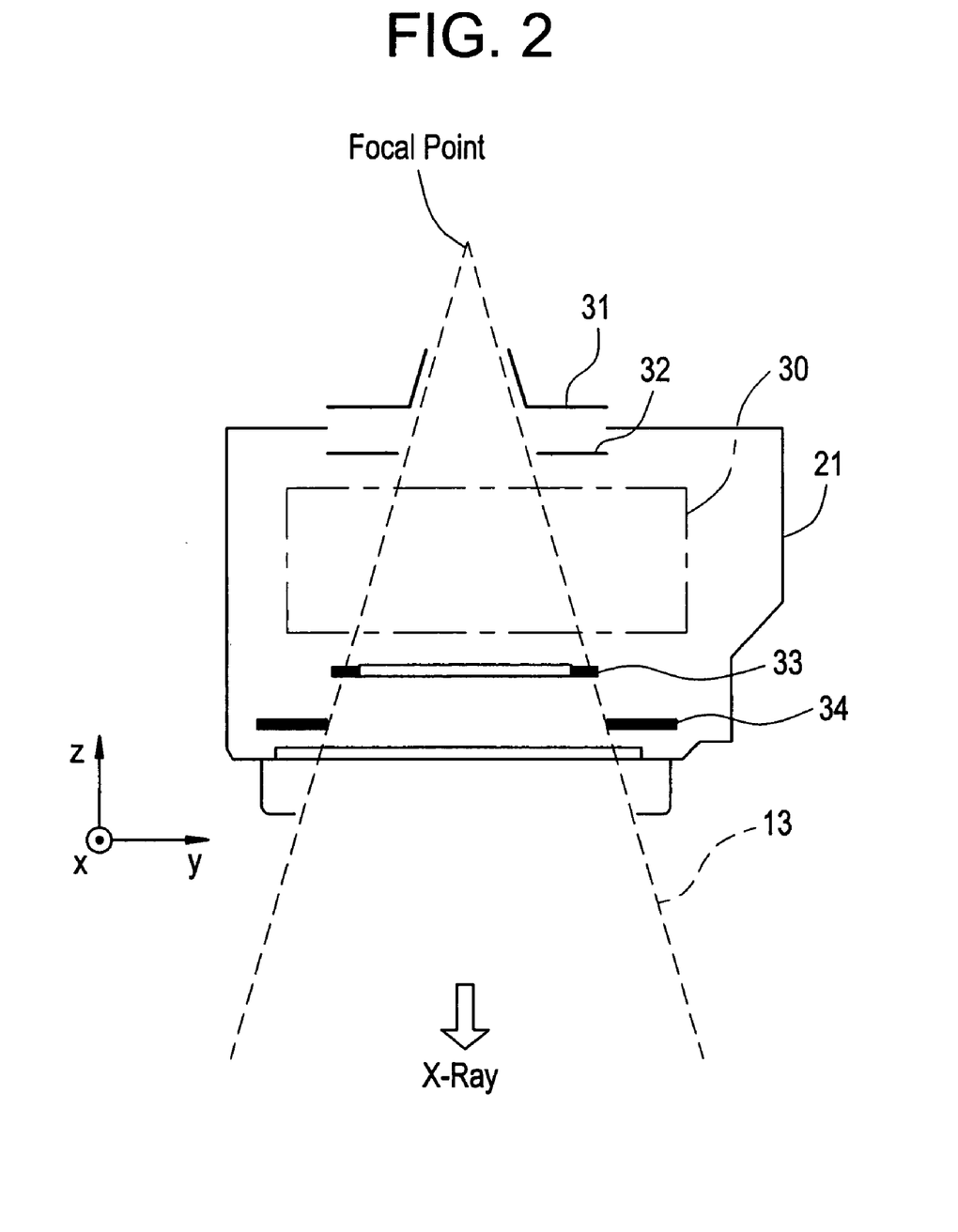
FIG. 2 is a sectional view showing the construction of a movable diaphragm according to an embodiment of the present invention.

FIG. 2 is a sectional view showing an example of the movable diaphragm 21. The movable diaphragm 21 includes an inner blade 31, a lower blade 32, a projector-collimator 30, and upper blades 33 and 34. The inner blade 31 and the lower blade 32 are formed of a material containing lead as a main component and functions to diminish X-ray which is out of focus, as well as scattered X-ray and leaking X-ray. The projector-collimator 30 emits a light beam for illuminating the X-ray irradiation field on the subject. The projector-collimator 30 emits the light beam in the X-ray radiating direction, i.e., in a negative z-axis direction. As to a concrete construction, a description will be given later. The upper blades 33 and 34 are formed of a material containing lead as a main component and function to restrict the X-ray irradiation field defined by the linear cone 13 into a minimum range required. The positions of the lower blade 32 and the upper blades 33, 34 are controlled to the x- or y-axis direction orthogonal to the X-ray radiating direction an arcuate drive using a gear or link mechanism (not shown) or by a parallel drive using a shaft.

Figure 3:
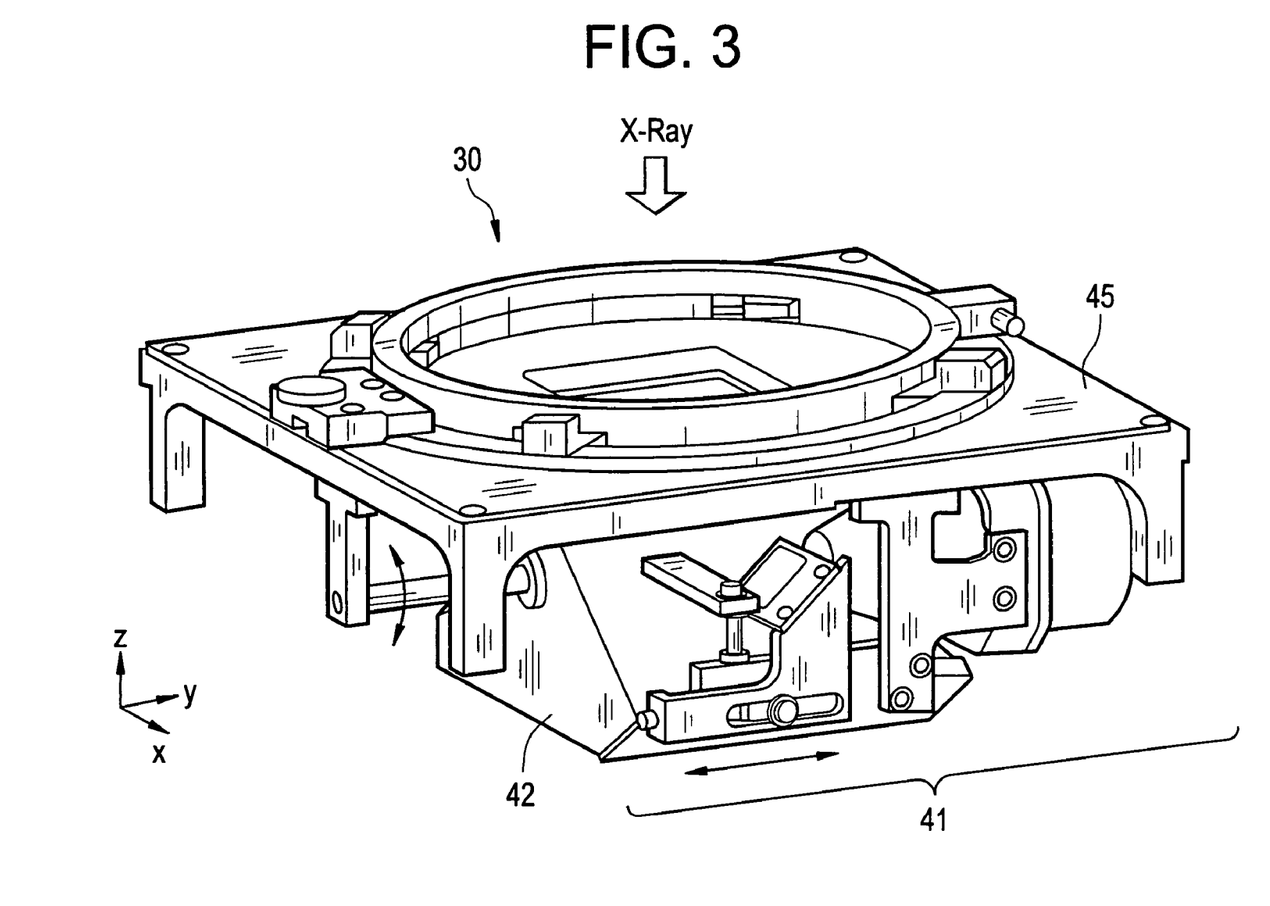
FIG. 3 is an appearance diagram showing an appearance of a projector-collimator used in the embodiment.

FIG. 3 is an appearance diagram showing an entire construction of the projector-collimator 30. The projector-collimator 30 includes a first reflecting section 41, a second reflecting section 42 and a third base. The first reflecting section 41 emits a first luminous flux in an orthogonal direction orthogonal to the X-ray radiating direction shown in FIG. 3, i.e., in the y-axis direction, and reflects the first luminous flux within an orthogonal plane orthogonal to the orthogonal direction, i.e., within the xz plane, to produce a second luminous flux. The second reflecting section 42 reflects the second luminous flux twice within the xz plane corresponding to the orthogonal plane to produce a light beam to be radiated to the subject 24. As to the first to third luminous fluxes, a description will be given later.

The third base 45 not only supports the first and second reflecting sections 41, 42 but also loads these reflecting sections to the movable diaphragm 21. The first reflecting section 41 is fixed to the third base indicated at 45 and the second reflecting section 42 is supported so as to be rotatable around y axis which is a direction orthogonal to the third base 45. The first and second reflecting sections 41, 42 are connected together mechanically through a second screw which will be described later.

Figure 4:
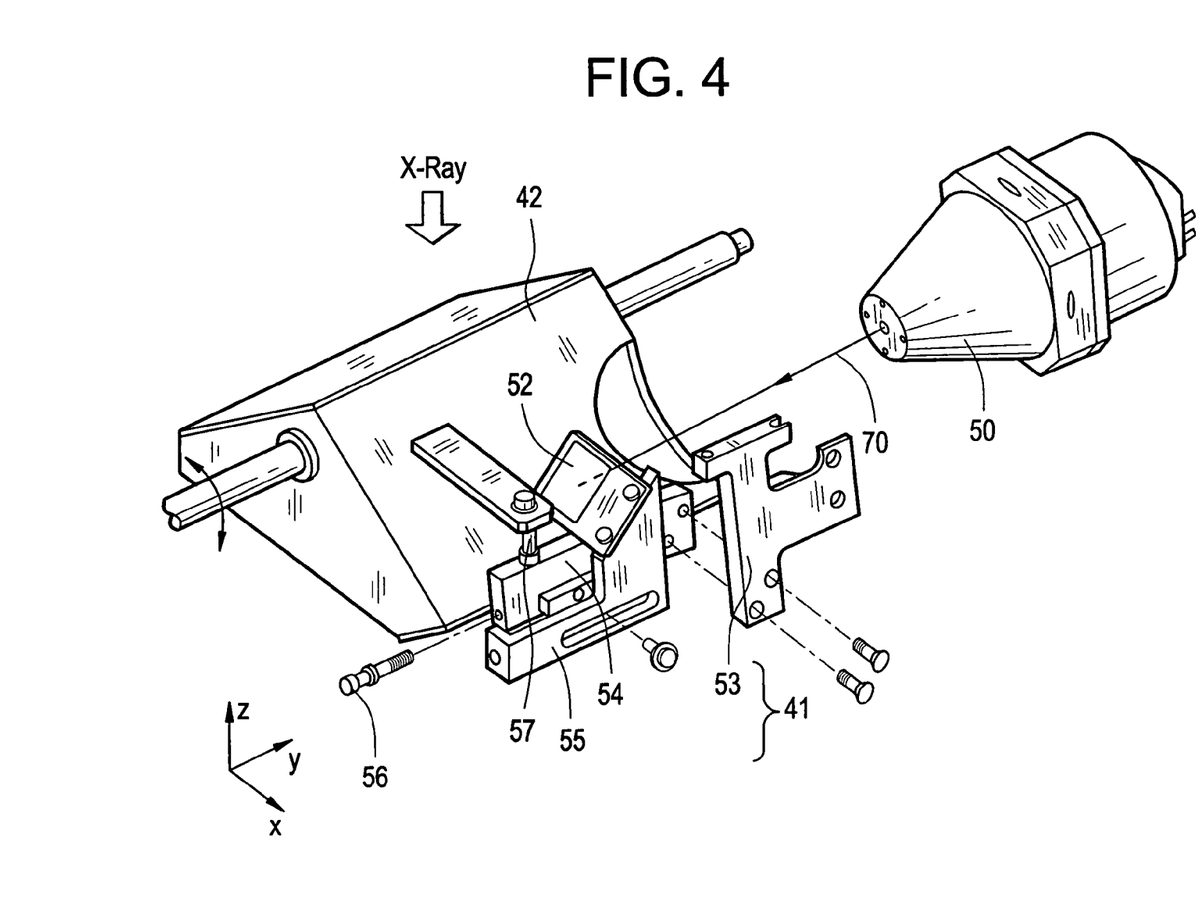
FIG. 4 is an exploded diagram showing the construction of a first reflecting section in the projector-collimator.

FIG. 4 is a combination of an exploded diagram showing the construction of the first reflecting section 41 with a diagram of the second reflecting section 42. The first reflecting section 41 includes a light source 50, a first mirror 52, first bases 53 and 54, a mirror support plate 55, a first screw 56, and a second screw 57. The light source 50 comprises a lamp of, for example, halogen which emits a first luminous flux in y-axis direction as the orthogonal direction, and is fixed to the first base 53 with use of screws for example. The first bases 53 and 54 are united using screws for example and at the same time the first base 53 is fixed to the third base 45 in the same manner. The first base 53 has tapped holes for threaded insertion therein of the first screw 56 as moving means in y-axis direction and the second screw 57 as rotating means around y axis.

The first mirror 52 reflects the first luminous flux which has been emitted in the orthogonal direction corresponding to the y-axis direction by the light source 50. The first mirror 52 reflects the first luminous flux within an orthogonal plane orthogonal to the orthogonal direction to produce a second luminous flux. The first mirror 52 has a reflecting surface positioned at an angle of 45° relative to the y-axis direction. This reflecting surface is moved in parallel in the y-axis direction by the mirror support plate 55 which supports the first mirror 52.

The first mirror 52 is secured to the mirror support plate 55, which in turn is secured to the first base 54 so as to be movable in the y-axis direction. The mirror support plate 55 shares the first screw 56 with the first base 54 in the y-axis direction which first screw is to be threadedly inserted in the y-axis direction into the first base 54. When the first screw 56 as moving means is threadedly inserted by a rotating motion thereof, the mirror support plate 55 changes a relative position thereof in the y-axis direction with respect to the first base 54. At the same time, the first mirror 52 secured to the mirror support plate 55 is also moved in the y-axis direction.

The first reflecting section 41 shares the second screw 57 with the second reflecting section 42 in the z-axis direction. The second screw 57 is to be threadedly inserted in the z-axis direction into the first base 54. When the second screw 57 as rotating means is threadedly inserted by a rotating motion thereof, the second reflecting section 42 changes a relative position thereof in the z-axis direction with respect to the first base 54 and eventually performs a rotating motion around the y-axis direction.

Figure 5:
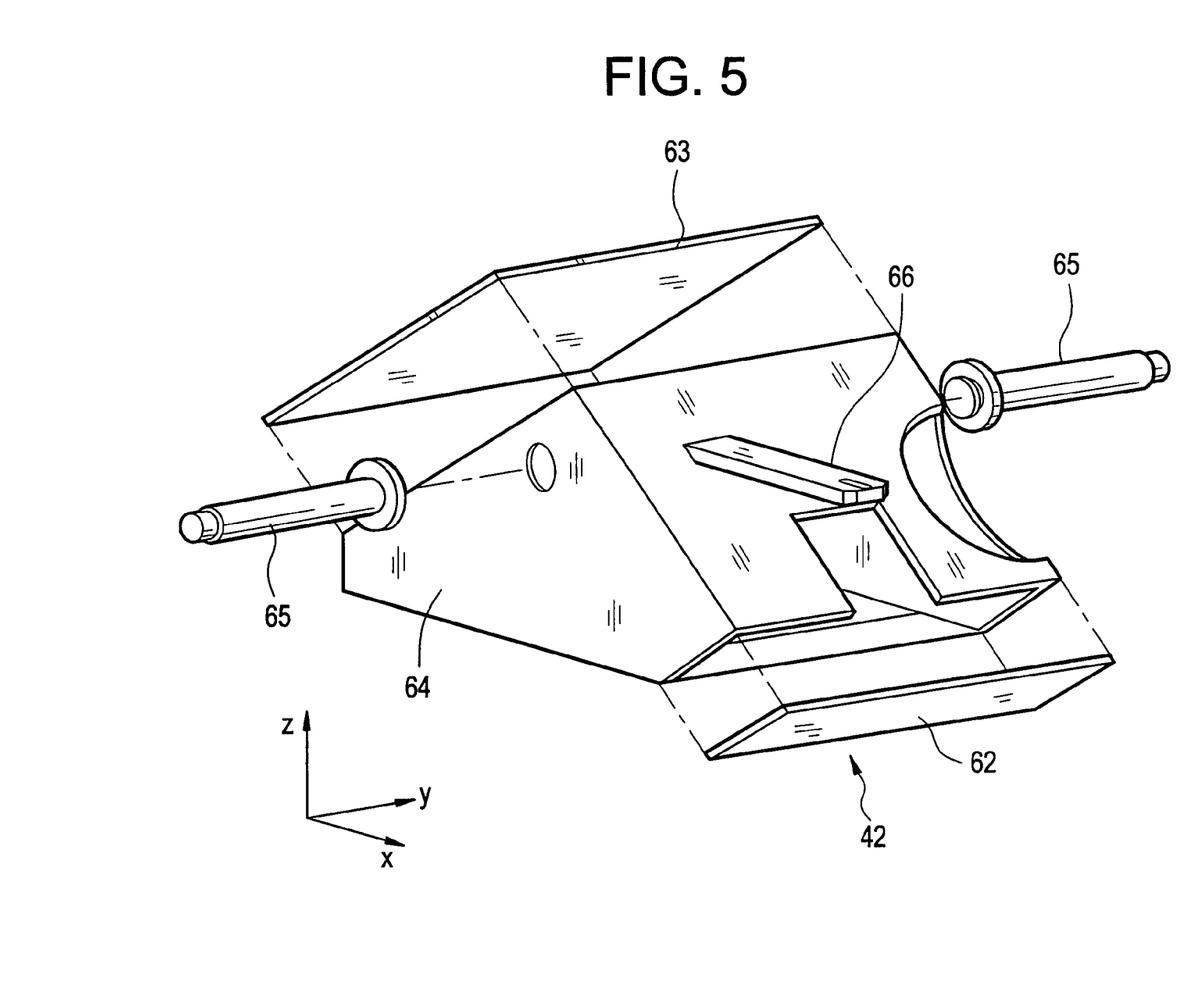
FIG. 5 is an exploded diagram showing the construction of a second reflecting section in the projector-collimator.

FIG. 5 is an exploded diagram showing the construction of the second reflecting section 42. The second reflecting section 42 includes a second mirror 62, a third mirror 63, a second base 64, a rotary shaft 65 and a connecting plate 66. The second mirror 62 reflects the second luminous flux reflected by the first mirror 52. The second mirror 62 is a light reflecting plate which reflects the second luminous flux toward the third mirror 63 located in the direction of the linear cone 13 to produce a third luminous flux. The third mirror 63 reflects the third luminous flux reflected by the second mirror 62. The third mirror 63 is a light reflecting plate reflecting the third luminous flux in the direction in which the subject 24 is present to produce a light beam. The third mirror 63 is set at such size and position as includes the linear cone 13 in its reflecting surface. The reflecting surface is formed using an X-ray transmitting material such as, for example, borosilicate glass.

The second base 64 is for supporting the second mirror 62 and the third mirror 63, which mirrors are bonded to the second base using, for example, an epoxy resin adhesive. The second base 64 has the rotary shaft 65 in the y-axis direction. The rotary shaft 65 is joined to a side face in the y-axis direction of the third base 45 by welding for example so as to permit rotation of the second reflecting section 42 around the y axis.

The second base 66 has the connecting plate 66 between the second mirror 62 and the third mirror 63. The connecting plate 66 is joined to the surface of the second base 64 by welding for example and has a tapped hole formed in an end portion thereof in the x-axis direction. The second screw 57 shown in FIG. 4 is threadedly inserted into the first base 54 through the tapped hole of the connecting plate 66. By rotating the second screw 57 to adjust the screwing depth, a relative distance between the first and second reflecting sections 41, 42 changes. Further, the first base 54 is fixed to the third base 45 and the second base 64 is supported by the third base 45 through the rotary shaft 65, so that by the above threaded insertion of the second screw the second base 64 rotates around the y axis.

Figure 6:
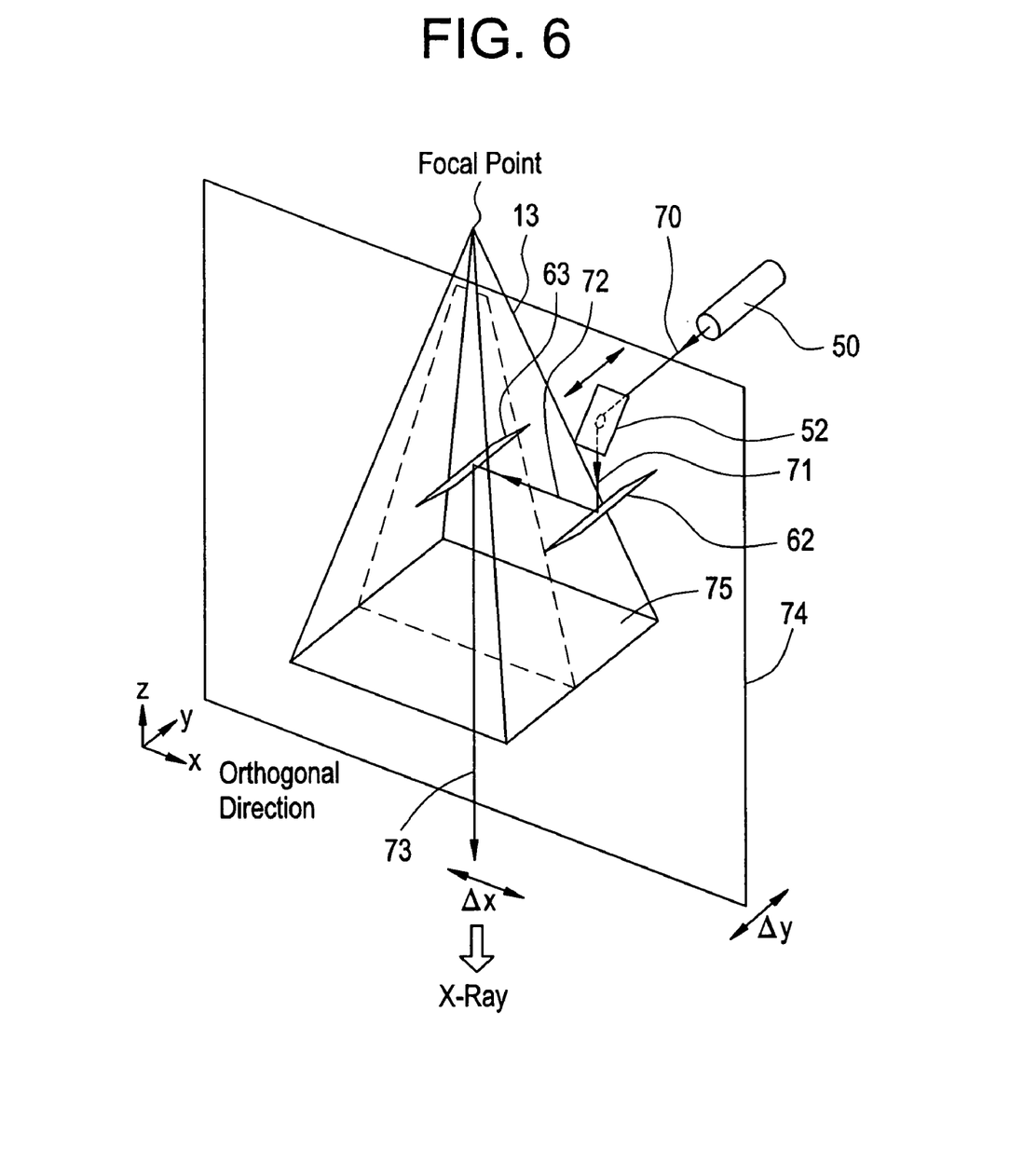
FIG. 6 is an explanatory diagram showing a traveling path of first to third luminous fluxes in the projector-collimator.

Next, the operation of the projector-collimator 30 associated with adjustment of the light beam position will be described with reference to FIGS. 6 to 8. FIG. 6 is an explanatory diagram illustrating only the first to third mirrors 52, 62, 63 from among the components of the projector-collimator 30 and also illustrating the foregoing first to third luminous fluxes and an optical axis portion of the light beam. Although the third mirror 63 is illustrated on a reduced scale for clearly showing its reflecting surface, it actually has a shape whose size includes the linear cone 13.

The linear cone 13 of X-ray emitted in the z-axis direction from a focal position has a rectangular irradiation field 75 spreading in both x- and y-axis directions. A first luminous flux 70 emitted from the light source 50 has an optical axis in the y-axis direction orthogonal to the X-ray radiating direction. The first luminous flux 70 is reflected by the first mirror 52 and there is produced a second luminous flux 71 within an orthogonal plane 74 orthogonal to the first luminous flux 70.

The second luminous flux 71 is reflected repeatedly within the orthogonal plane 74 by the second and third mirrors 62, 63 to produce a third luminous flux 72 and a light beam 73. The orthogonal plane 74 is a plane parallel to the xz plane and positioned near a focal point. A broken line within the linear cone shown in FIG. 6 represents an intersecting position between the linear cone 13 and the orthogonal plane 74. A y-axis position of the orthogonal plane 74 is moved by moving the position of the first mirror 52 in the y-axis direction through the first screw 56. At the same time, the second luminous flux 71, the third luminous flux 72 and the light beam 73 are also moved in the y-axis direction.

Figure 7:
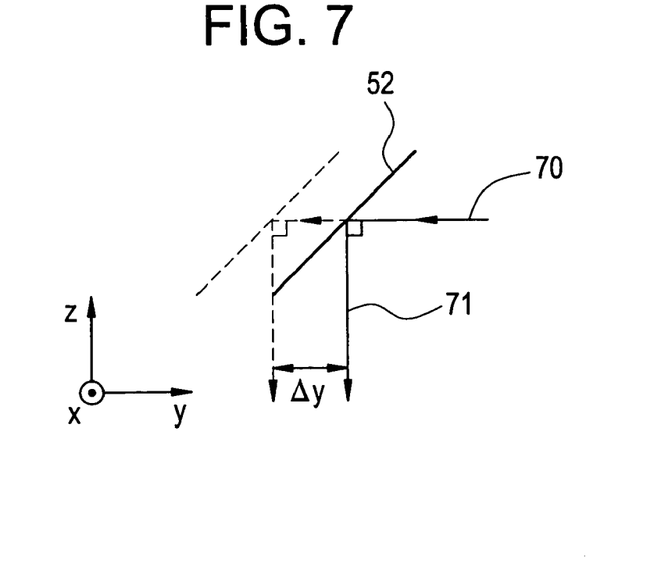
FIG. 7 is an explanatory diagram showing the operation of a first mirror in the projector-collimator.

FIG. 7 is an explanatory diagram of the first mirror 52 as seen in the x-axis direction. The first mirror 52 is moved by only Δy in the y-axis direction by the first screw 56. At this time, the second luminous flux 71 reflected by the first mirror 52 is also moved by only Δy in the y-axis direction. Further, the orthogonal plane 74 including the second luminous flux 71 moves by only Δy in the y-axis direction. The second mirror 62 and the third mirror 63 for reflecting the second luminous flux 71 and the third luminous flux 72 are each provided with a rectangular reflecting plate having long sides in the y-axis direction lest the optical axis of reflected light should deviate from the reflecting surface with movement of the first mirror 52.

Referring back to FIG. 6, the second mirror 62 and the third mirror 63 for reflecting the second luminous flux 71 and the third luminous flux 72 are rotated around the y axis together with the second base 64 by means of the second screw 57. In this case, the long sides of the rectangular reflecting surfaces of the second and third mirrors 62, 63 are disposed in the y-axis direction, i.e., in the same direction as the first luminous flux 70, so that even if the aforesaid rotation is performed, the third luminous flux and the light beam 73 are held within the orthogonal plane74.

Figure 8:
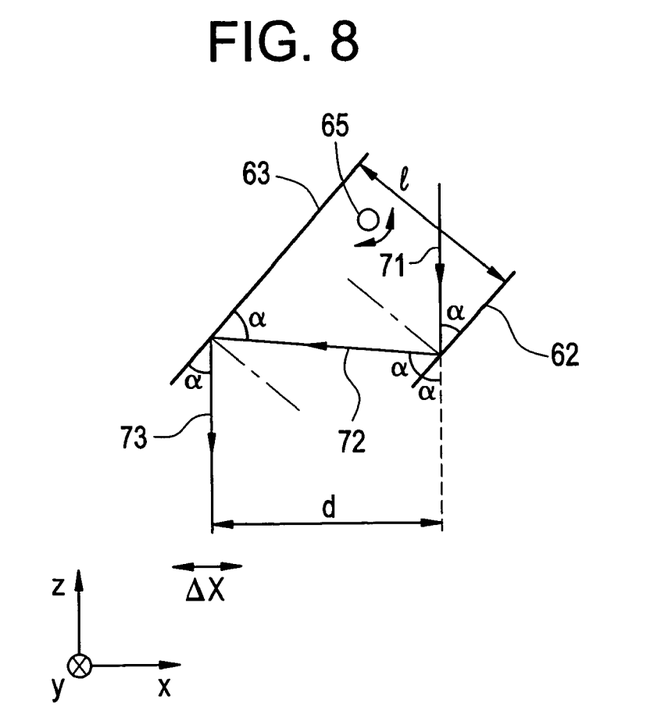
FIG. 8 is an explanatory diagram showing the operation of second and third mirrors in the projector-collimator.

FIG. 8 is an explanatory diagram of the second and third mirrors 62, 63 as seen in the y-axis direction. The second and third mirrors 62, 63 are disposed so that their light reflecting surfaces are parallel to each other, and are rotated around the y axis by the second base 64 as a common base. With this rotation, the second luminous flux 71 and the light beam 73 move in parallel in the light traveling direction without changing the traveling direction itself.

Given that a parallel movement distance in the light traveling direction is d, the distance between the parallel second and third mirrors 62, 63 is 1 and an incidence angle of the second luminous flux 71 relative to the second mirror 62 is a, the following relationship is established:

$$d = 2 * 1 * \cos(a)$$

In accordance with the above relationship, the incidence angle (a) is changed by rotation of the second base 64 and hence the parallel movement distance (d) of the second luminous flux 71 and the light beam 73 is changed, and the position in the x-axis direction within the irradiation field of the light beam 73 is changed by only Δx corresponding to the amount of change of (d). With this rotation, the third luminous flux 72 and the light beam 73 do not change their positions in the y-axis direction.

In this embodiment, as described above, the first luminous flux 70 is made a luminous flux present within the orthogonal plane 74 orthogonal to the y-axis direction which is the orthogonal direction, and the second luminous flux present within the orthogonal plane 74 is reflected and moved within the orthogonal plane 74 to produce the light beam 73, so that the irradiation position of the light beam 73 on the subject can be adjusted in an independent manner by the movement Δy in the orthogonal direction by the first screw 56 and the movement Δx within the orthogonal plane 74 by the second screw 57. Consequently, adjustment of the X-ray irradiation field position by the operator can be effected easily and with a high accuracy.

Although in this embodiment the irradiation field of the linear cone 13 is rectangular, also in the case of an irradiation field of a circular or any other shape, the position of the light beam 73 in the x-axis direction and that in the y-axis direction can also be adjusted in just the same manner.

Although in this embodiment the FPD 23 is used as an X-ray detector, it may be substituted by, for example, X-ray film, imaging plate, or imaging intensifier, whereby it is possible to obtain transmitted image information on the subject 24.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An X-ray imaging apparatus comprising:
an X-ray source for radiating X-ray to a subject;
a movable diaphragm for adjusting an irradiation field of the X-ray; and
a projector-collimator installed within said movable diaphragm to project a light beam to an irradiation field position on the subject, said projector-collimator comprising:
a first reflecting section comprising a first mirror, said first reflecting section positioned outside the irradiation field, said first reflecting section producing a first luminous flux in a first direction orthogonal to an X-ray radiating direction and reflecting the first luminous flux within a plane orthogonal to the first direction to produce a second luminous flux, said first mirror moveable in the first direction to adjust a length of the first luminous flux; and
a second reflecting section comprising a second mirror and a third mirror, said second reflecting section reflecting the second luminous flux in a direction of the irradiation field within the plane to produce a third luminous flux and reflecting the third luminous flux in the X-ray radiating direction inside the irradiation field within the plane to produce the light beam, said second mirror and said third mirror concurrently rotatable about the first direction to adjust a length of the third luminous flux.

2. An X-ray imaging apparatus comprising:
an X-ray source for radiating X-ray to a subject;
a movable diaphragm for adjusting an irradiation field of the X-ray; and
a projector-collimator installed within said movable diaphragm to project a light beam to an irradiation field position on the subject, said projector-collimator comprising:
a first reflecting section which is positioned outside the irradiation field, said first reflecting section produces a first luminous flux in an orthogonal direction orthogonal to the X-ray radiating direction and reflects the first luminous flux within an orthogonal plane orthogonal to the orthogonal direction to produce a second luminous flux, a length of the first luminous flux controlled by moving said first reflecting section in the orthogonal direction; and
a second reflecting section which reflects the second luminous flux in the direction of the irradiation field within the orthogonal plane to produce a third luminous flux and reflects the third luminous flux in the X-ray radiating direction inside the irradiation field within the orthogonal plane to produce the light beam, a length of the third luminous flux controlled by rotating said second reflecting section in the orthogonal direction.

3. An X-ray imaging apparatus according to claim 2, wherein said first reflecting section comprises a light source for producing the first luminous flux, a first mirror for producing the second luminous flux from the first luminous flux, and a first base for disposing said light source and said first mirror thereon.

4. An X-ray imaging apparatus according to claim 3, wherein said light source comprises a halogen lamp.

5. An X-ray imaging apparatus according to claim 3, wherein said first base comprises a moving means for moving said first mirror in the orthogonal direction.

6. An X-ray imaging apparatus according to claim 5, wherein said moving means comprises a first screw for changing relative positions in the orthogonal direction of said first base and a mirror support plate for supporting said first mirror.

7. An X-ray imaging apparatus according to claim 5, wherein said moving means, during the movement, does not change an inclination of said first mirror in the orthogonal direction.

8. An X-ray imaging apparatus according to claim 1, wherein said second reflecting section comprises a second mirror for producing the third luminous flux from the second luminous flux, a third mirror for producing the light beam from the third luminous flux and transmitting the X-ray, and a second base for disposing said second mirror and said third mirror fixedly thereon.

9. An X-ray imaging apparatus according to claim 8, wherein said second base comprises a rotating means for performing a slight rotation around the orthogonal direction.

10. An X-ray imaging apparatus according to claim 9, wherein said rotating means comprises a second screw for changing relative rotations of said second base and said first base.

11. An X-ray imaging apparatus according to claim 8, wherein said second mirror comprises a reflecting surface for the second luminous flux positioned outside the irradiation field.

12. An X-ray imaging apparatus according to claim 8, wherein said third mirror comprises a reflecting surface for reflecting the third luminous flux at a size and a position including the X-ray irradiation field.

13. An X-ray imaging apparatus according to claim 8, wherein said second mirror and said third mirror are disposed in parallel with each other.

14. An X-ray imaging apparatus according to claim 8, wherein said second mirror and said third mirror each have a rectangular shape having long sides in the orthogonal direction.

15. An X-ray imaging apparatus according to claim 6, wherein said projector-collimator further comprises a third base for supporting said first base and said second base.

16. An X-ray imaging apparatus according to claim 8, wherein said projector-collimator further comprises a third base for supporting said first base and said second base.

17. An X-ray imaging apparatus according to claim 15, wherein said second base comprises a rotary shaft extending in the orthogonal direction and supported by said third base.

18. An X-ray imaging apparatus according to claim 16, wherein said second base comprises a rotary shaft extending in the orthogonal direction and supported by said third base.

19. An X-ray imaging apparatus according to claim 15, wherein said first base is fixedly coupled to said third base.

20. An X-ray imaging apparatus according to claim 16, wherein said first base is fixedly coupled to said third base.

* * * * *